(12) United States Patent
Chung et al.

(10) Patent No.: US 6,620,824 B2
(45) Date of Patent: Sep. 16, 2003

(54) PROCESS FOR THE SYNTHESIS OF GONADOTROPIN RELEASING HORMONE ANTAGONISTS

(75) Inventors: John Y. L. Chung, Edison, NJ (US); Roger N. Farr, Whitehouse Station, NJ (US); Guy R. Humphrey, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/117,657

(22) Filed: Apr. 5, 2002

(65) Prior Publication Data

US 2003/0013876 A1 Jan. 16, 2003

Related U.S. Application Data

(60) Provisional application No. 60/283,049, filed on Apr. 11, 2001.

(51) Int. Cl.[7] ............. A61K 31/4439; C07D 401/12
(52) U.S. Cl. .............. 514/339; 546/277.4; 546/164; 546/193; 548/511; 514/339
(58) Field of Search ............. 546/277.4, 193, 546/164; 514/339; 548/511, 965

(56) References Cited

U.S. PATENT DOCUMENTS

| | | | |
|---|---|---|---|
| 4,252,803 A | 2/1981 | Webb | |
| 4,544,663 A | 10/1985 | Manning et al. | |
| 5,030,640 A | 7/1991 | Fisher et al. | |
| 5,849,764 A | * 12/1998 | Goulet et al. ........... | 514/337 |

FOREIGN PATENT DOCUMENTS

| | | |
|---|---|---|
| BE | 879381 | 2/1980 |
| EP | 0 219 292 | 4/1987 |
| EP | 0 679 642 | 11/1995 |
| FR | 2181559 | 12/1973 |
| WO | WO 90/05721 | 5/1990 |
| WO | WO 95/28405 | 10/1995 |
| WO | WO 95/29900 | 11/1995 |

OTHER PUBLICATIONS

De, B. et al., J. Med. Chem., 32, 2036–2038 (1989).

* cited by examiner

*Primary Examiner*—Alan L. Rotman
*Assistant Examiner*—Janet L Coppins
(74) *Attorney, Agent, or Firm*—Valerie J. Camara; Mark R. Daniel

(57) ABSTRACT

The present invention relates to a process for preparing a compound of gonadotropin releasing hormone antagonists having a Formula I,

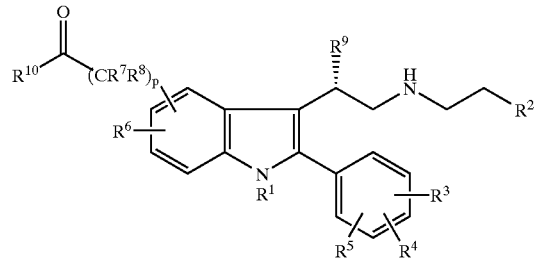

in an efficient way, which involves preparation of key intermediates: 2-arylindole core; a chiral aziridine, in particular chiral nosyl aziridine; and an amine salt. The key process involves the coupling reaction of 2-arylindole and nosyl aziridine under boron trifluoride catalysis, which provides the final compound with unprecedented regioselectivity and enantioselectivity.

28 Claims, No Drawings

PROCESS FOR THE SYNTHESIS OF GONADOTROPIN RELEASING HORMONE ANTAGONISTS

This application claims the benefit of provisional application No. 60/283,049 filed Apr. 11, 2001.

FIELD OF THE INVENTION

The present invention is directed to a process for preparing a gonadotropin releasing hormone antagonist having an arylindole core.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females.

GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral administration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. Fisher et al. (U.S. Pat. No. 5,030,640) discloses alpha-heterocyclic ethanol aminoalkyl indoles which are potent β-agonists.

Manning et al. (U.S. Pat. No. 4,544,663) is directed to indolamine derivatives which can be used as male anti-fertility agents.

Youngdale et al (WO 90/0572) discloses alpha-amino-indole-3-acetic acids useful as anti-diabetic, anti-obesity and anti-atherosclerotic agents.

Boch et al. (French pat. No. 2,181,559) discloses indole derivatives with sedative, neuroleptic, analgesic, hypotensive, antiserotonin and adrenolytic activity.

Belgian patent 879381 discloses 3-aminoalkyl-1H-indole-5-thioamide and carboxamide derivatives as cardiovascular agents used to treat hypertension, Raynaud's disease and migraine.

An object of the present invention is to develop an efficient synthetic route to prepare the class of GnRH antagonist compounds having regioselectivity and enantioselectivity, specifically the class of compound known as chiral tryptamines.

SUMMARY OF THE INVENTION

The present invention is directed a process for preparing a compound of Formula I,

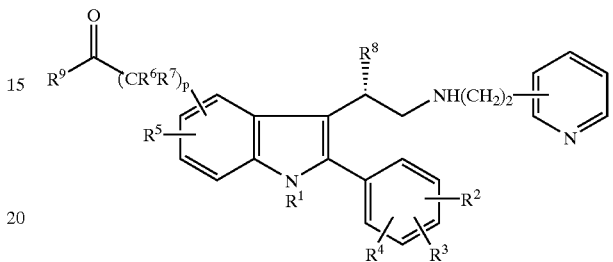

I or its pharmaceutically acceptable salt, hydrate or solvate thereof, wherein:

p is: 1–4;

$R^1$ is:
(1) hydrogen,
(2) $(C_1-C_6)$-alkyl, or
(3) aryl;

$R^2$, $R^3$, and $R^4$ are independently:
(1) hydrogen,
(2) $(C_1-C_6)$-alkyl,
(3) $(C_2-C_6)$-alkenyl,
(4) CN,
(5) nitro,
(6) $(C_1-C_3)$-perfluoroalkyl,
(7) $(C_1-C_3)$-perfluoroalkoxy, or
(8) aryl;

$R^5$ is:
(1) hydrogen,
(2) $(C_1-C_6)$-alkyl,
(3) aryl,
(4) $(C_1-C_3)$-perfluoroalkyl,
(5) CN,
(6) $NO_2$, or
(7) halogen;

$R^6$ and $R^7$ are independently:
(1) hydrogen, or
(2) $(C_1-C_6)$-alkyl;

$R^8$ is:
(1) $(C_1-C_6)$-alkyl; or
(2) aryl; and $R^9$ is:
(1) $(C_1-C_6)$-alkoxy, or
(2) $NHR^{10}R^{11}$, wherein $R^{10}$ and $R^{11}$ are independently:
(a) hydrogen,
(b) $(C_1-C_6)$-alkyl, or
(c) aryl,
wherein $R^{10}$ and $R^{11}$ taken together form a monocyclic ring, bicyclic ring or bridged ring containing from 3 to 7 carbon atoms, and the ring may be optionally substituted by $R^2$, $R^3$, and $R^4$; and $R^{12}$ is:

(1) $(C_1-C_6)$-alkyl, (2) halo, wherein halo is F, Cl, Br or I, (3) $(C_1-C_4)$-perfluoroalkyl, (4) $(CH_2)_n NMe_3^+$ wherein n is 1 to 6, or (5) aryl wherein aryl is optionally substituted with one, two, or three substituents selected from the group consisting of $NO_2$, $(C_1-C_6)$-alkyl, and halo as defined above;

comprising the steps of:

(1) reacting a compound of formula (a),

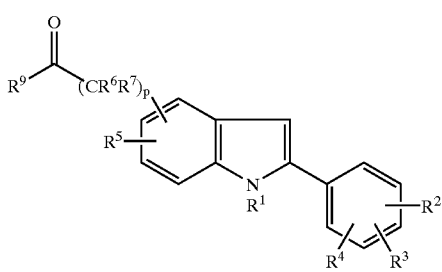

with an aziridine compound of formula

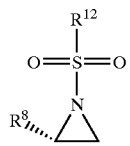

in the presence of a Lewis-acid in an aprotic solvent to produce a compound of formula (b)

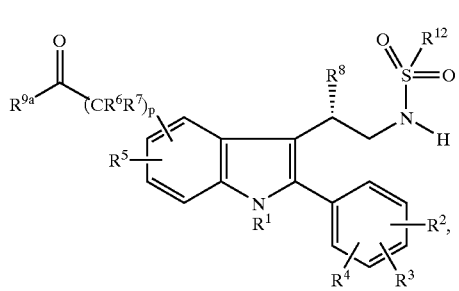

wherein $R^{9a}$ is $(C_1-C_6)$-alkoxy, hydrolyzing the compound of formula (b) in the presence of a base and a protic solvent to give an acid form of the compound of formula (b) wherein $R^{9a}$ is hydroxyl;

(2) reacting the acid form of the compound of formula (b) with an amine in an aprotic solvent to produce a compound of formula (c)

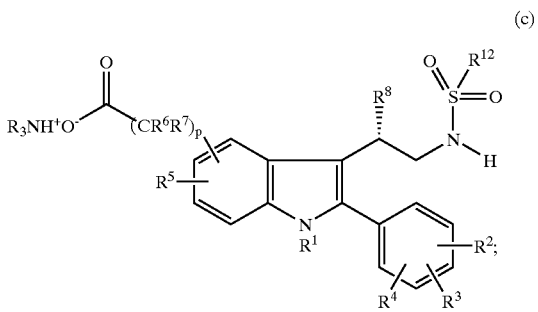

(3) reacting the compound of formula (c) with amine, $NHR^{10}R^{11}$ in the presence of a base in an aprotic solvent to give an amide compound of formula (d),

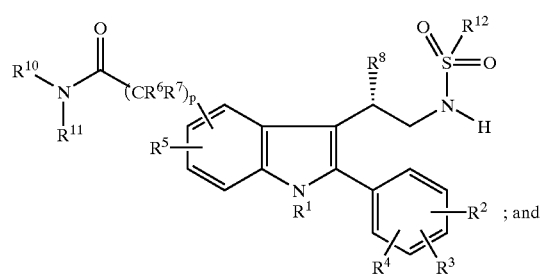

(4) reacting the compound of formula (d) with

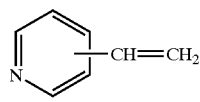

in the presence of an acid in an aprotic solvent to give the compound of Formula I.

DETAILED DESCRIPTION OF THE INVENTION

The present invention relates to a process for the synthesis of a gonadotropin releasing hormone antagonist in an efficient way, which involves preparation of key intermediates: 2-arylindole core; a chiral aziridine, in particular chiral nosyl aziridine; and an amine salt. The key step in the process is the coupling reaction of 2-arylindole and nosyl aziridine using boron trifluoride catalysis. The process of the present invention provides the compound of Formula I with unprecedented regioselectivity and enantioselectivity.

The present invention relates to a process for preparing a compound of Formula I,

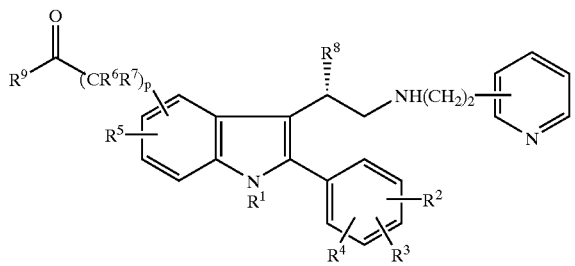

or its pharmaceutically acceptable salt, hydrate or solvate thereof, wherein:
p is: 1–4;
$R^1$ is:
  (1) hydrogen,
  (2) $(C_1-C_6)$-alkyl, or
  (3) aryl;
$R^2$, $R^3$, and $R^4$ are independently:
  (1) hydrogen,
  (2) $(C_1-C_6)$-alkyl,
  (3) $(C_2-C_6)$-alkenyl,
  (4) CN,
  (5) nitro,
  (6) $(C_1-C_3)$-perfluoroalkyl,
  (7) $(C_1-C_3)$-perfluoroalkoxy, or
  (8) aryl;
$R^5$ is:
  (1) hydrogen,
  (2) $(C_1-C_6)$-alkyl,
  (3) aryl,
  (4) $(C_1-C_3)$-perfluoroalkyl,
  (5) CN,
  (6) $NO_2$, or
  (7) halogen;
$R^6$ and $R^7$ are independently:
  (1) hydrogen, or
  (2) $(C_1-C_6)$-alkyl;
$R^8$ is:
  (1) $(C_1-C_6)$-alkyl; or
  (2) aryl; and
$R^9$ is:
  (1) $(C_1-C_6)$-alkoxy, or
  (2) $NHR^{10}R^{11}$, wherein $R^{10}$ and $R^{11}$ are independently:
    (a) hydrogen,
    (b) $(C_1-C_6)$-alkyl, or
    (c) aryl,
    wherein $R^{10}$ and $R^{11}$ taken together form a monocyclic ring, bicyclic ring or bridged ring containing from 3 to 7 carbon atoms, and the ring may be optionally substituted by $R^2$, $R^3$, and $R^4$; and
$R^{12}$ is:
  (1) $(C_1-C_6)$-alkyl,
  (2) halo, wherein halo is F, Cl, Br or I,
  (3) $(C_1-C_4)$-perfluoroalkyl,
  (4) $(CH_2)_n NMe_3^+$ wherein n is 1 to 6, or
  (5) aryl wherein aryl is optionally substituted with one, two, or three substituents selected from the group consisting of $NO_2$, $(C_1-C_6)$-alkyl, and halo as defined above;

comprising the steps of:
(1) reacting a compound of formula (a),

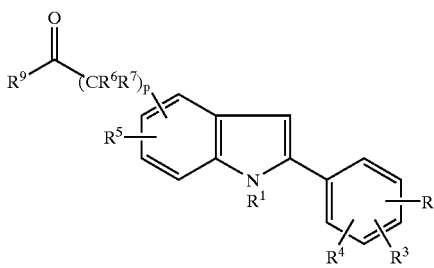

with an aziridine compound of formula

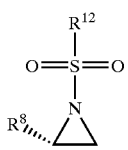

in the presence of a Lewis-acid in an aprotic solvent to produce a compound of formula (b)

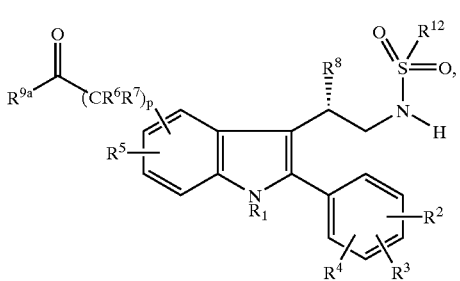

wherein $R^{9a}$ is $(C_1-C_6)$-alkoxy, hydrolyzing the compound of formula (b) in the presence of a base and a protic solvent to give an acid form of the compound of formula (b) wherein $R^{9a}$ is hydroxyl;

(2) reacting the acid form of the compound of formula (b) with an amine in an aprotic solvent to produce a compound of formula (c)

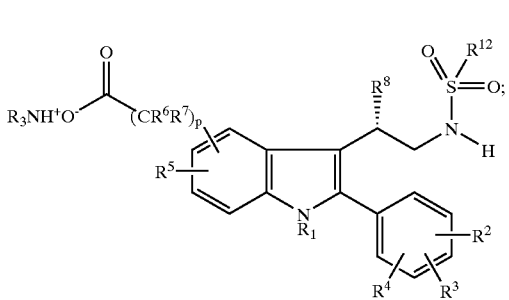

(3) reacting the compound of formula (c) with amine, $NHR^{10}R^{11}$ in the presence of a base in an aprotic solvent to give an amide compound of formula (d),

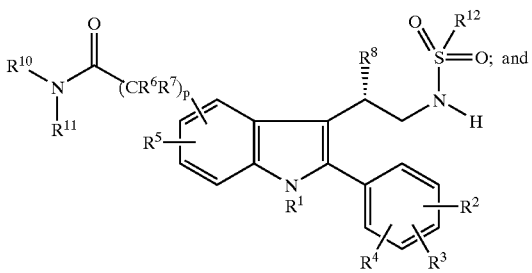

(d)

(4) reacting the compound of formula (d) with

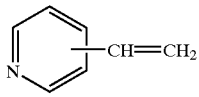

in the presence of an acid in an aprotic solvent to give the compound of Formula I.

The process as recited above, wherein the aprotic solvent is selected from the group consisting of: isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof.

The process as recited above, wherein the aziridine is a nosyl aziridine of formula

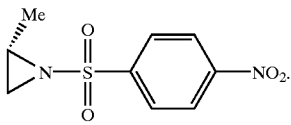

The process as recited above, wherein a temperature range for the step (1) reaction is between about 0° C. and about 60° C.

The process as recited above, wherein the Lewis acid in step (1) is selected from the group consisting of group consisting of $BF_3$—$OEt_2$, $BX_3$, $SnX_2$, and $SnX_4$ wherein X is halo. The preferred Lewis acid is $BF_3$—$OEt_2$.

The process as recited above, wherein the base in step (1) is selected from the group consisting of sodium hydroxide, lithium hydroxide, potassium hydroxide, calcium hydroxide, lithium methoxide, sodium methoxide, potassium methoxide, lithium ethoxide, sodium ethoxide, potassium ethoxide, lithium tert-butoxide, sodium tert-butoxide, and potassium tert-butoxide. The preferred base is sodium hydroxide.

The process as recited above, wherein the protic solvent is selected from the group consisting of $(C_1-C_6)$-alcohol, $H_2O$ or mixtures thereof. The preferred protic solvent is ethanol.

The process as recited above, wherein the amine in step (2) is $NH_3$, $NHR_2$ or $NR_3$ wherein R is $(C_1-C_6)$-alkyl, which is selected from the group consisting of methylamine, ethylamine, propylamine, isopropylamine, butylamine, isobutylamine, sec-butylamine, n-tributylamine, tert-butylamine, dimethylamine, diethylamine, dipropylamine, trimethylamine, and triethylamine, tripropylamine, and tributylamine. The preferred amine is n-tributylamine.

The process as recited above, wherein the base in step (3) is selected from the group consisting of tert-butylamine, trimethylamine, triethylamine, tripropylamine, and tributylamine, tetramethyl piperidine, hexamethyldisilazane, sodium carbonate, potassium carbonate, cesium carbonate, sodium bicarbonate, potassium bicarbonate, sodium hydroxide, potassium hydroxide, calcium hydroxide and cesium hydroxide. The preferred base is triethylamine.

The process as recited above wherein the acid in step (4) is selected from the group consisting of triethylamine hydrochloride, phenol, $(C_1-C_6)$-alkanoic acid, $(C_1-C_6)$-alkanoic diacid, and $(C_1-C_6)$-alkanoic triacid each having a pKa less than 7. The preferred acid is acetic acid.

The process as recited above, wherein

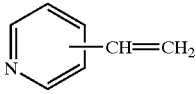

is present in amounts between about 4 equivalents and about 6 equivalents.

The process as recited above, wherein the step (3) reaction initially further comprises the steps of:

(i) breaking the salt compound of formula (c) wherein $R^{9a}$ is $O^-NHR_3^+$ using citric acid in an aprotic solvent to form a free acid of formula (c) wherein $R^{9a}$ is OH; and (ii) reacting the free acid compound of formula (c) with a chlorinating agent in an aprotic solvent to form an acid chloride compound of formula (c) wherein $R^{9a}$ is Cl.

The process as recited above, wherein the chlorinating agent is $SOCl_2$, oxalyl chloride, carbon tetrachloride, and triphenylphosphine dichloride. The preferred chlorinating agent is $SOCl_2$.

The process as recited above, wherein the step (4) reaction initially further comprises deprotecting —$S(O)_2$—$R^{12}$ group of the compound of formula (d) using a mercaptan source and a base in a protic solvent to form the free amine compound of formula (d),

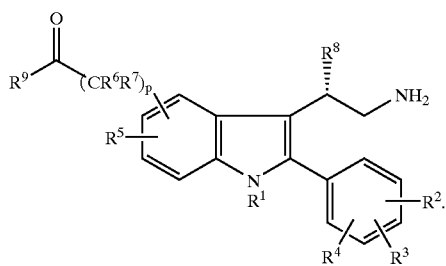

The process as recited above, wherein the mercaptan source is selected from the group consisting of n-dodecanethiol, thiophenol, and mercaptoacetic acid. The preferred mercaptan source is n-dodecanethiol.

The process as recited above, wherein the base used for deprotecting —$S(O)_2$—$R^{12}$ group is sodium hydroxide, lithium hydroxide, potassium hydroxide, calcium hydroxide, lithium methoxide, sodium methoxide, potassium methoxide, calcium methoxide, lithium ethoxide, sodium ethoxide, potassium ethoxide, lithium tert-butoxide, sodium tert-butoxide, potassium tert-butoxide, sodium carbonate, potassium carbonate, cesium carbonate, sodium bicarbonate, and potassium bicarbonate. The preferred base is lithium hydroxide.

A preferred embodiment of the present invention is a process for preparing a compound of Formula I'

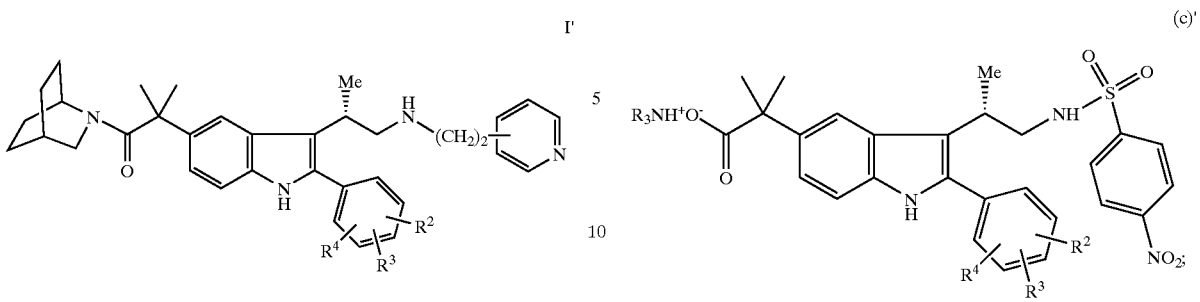

or pharmaceutically acceptable salt, hydrate, or solvate thereof, wherein $R^2$, $R^3$, and $R^4$ are independently hydrogen or $(C_1–C_6)$-alkyl; comprising the steps of:

(1) reacting a compound of formula (a)'

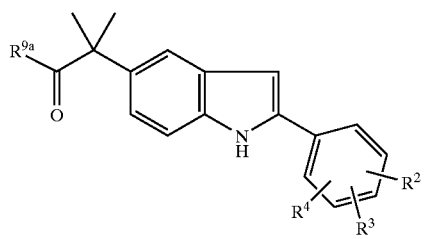

wherein $R^{9a}$ is $OCH_3$, with a nosyl aziridine of formula

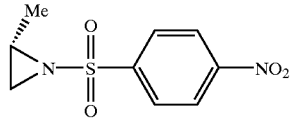

in the presence of a Lewis-acid in an aprotic solvent to produce a compound of formula (b)'

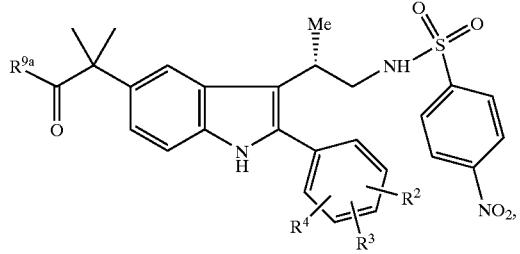

hydrolyzing the compound of formula (b)' in the presence of a base and a protic solvent to give an acid form of the compound of formula (b)' wherein $R^{9a}$ is hydroxyl;

(2) reacting the acid form of the compound of formula (b)' with n-tributylamine in an aprotic solvent to produce a compound of formula (c)'

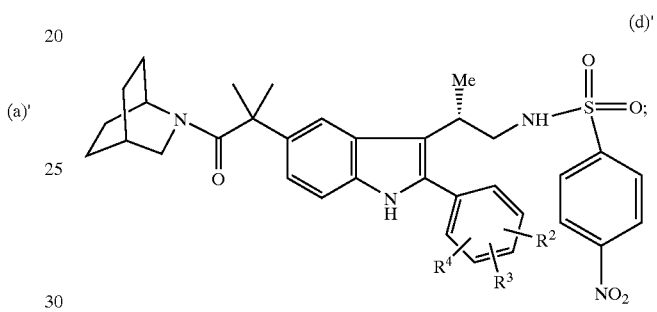

(3) reacting the compound of formula (c)' with isoquinuclidine in the presence of a base in an aprotic solvent to give an amide isoquinuclidinyl compound of formula (d)'

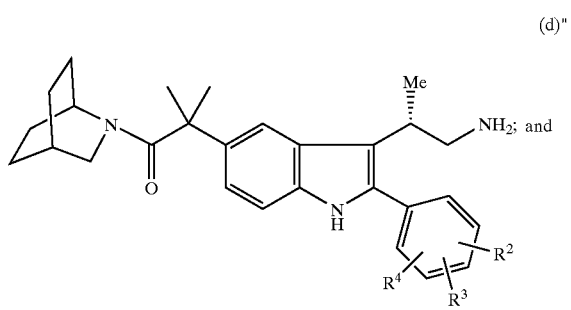

(4) deprotecting nosyl protected amine of formula (d)' in the presence of n-dodecanethiol, a base, and a protic solvent to give a free amine of formula (d)'',

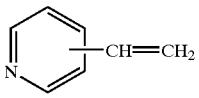

(5) reacting the free amine of formula (d)'' with

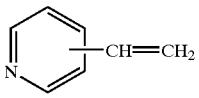

in the presence of an acid in an aprotic solvent to give the compound of Formula I'.

The process as recited above, wherein the aprotic solvent is selected from the group consisting of isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof.

The process as recited above, wherein a temperature range for the step (1) reaction is between about 0° C. and about 60° C.

The process as recited above, wherein the Lewis acid in step (1) is selected from the group consisting of $BF_3$—$OEt_2$, BX$_3$, SnX$_2$, and SnX$_4$ wherein X is halo. The preferred Lewis acid is BF$_3$—OEt$_2$.

The process as recited above, wherein the base in step (1) is selected from the group consisting of sodium hydroxide, lithium hydroxide, potassium hydroxide, calcium hydroxide, lithium methoxide, sodium methoxide, potassium methoxide, lithium ethoxide, sodium ethoxide, potassium ethoxide, lithium tert-butoxide, sodium tert-butoxide, and potassium tert-butoxide. The preferred base is sodium hydroxide.

The process as recited above, wherein the protic solvent is selected from the group consisting of (C$_1$–C$_6$)-alcohol, H$_2$O or mixtures thereof. The preferred protic solvent is ethanol.

The process as recited above, wherein the base in step (3) is selected from the group consisting of tert-butylamine, trimethylamine, triethylamine, tripropylamine, and tributylamine, tetramethyl piperidine, hexamethyldisilazane, sodium carbonate, potassium carbonate, cesium carbonate, sodium bicarbonate, potassium bicarbonate, sodium hydroxide, potassium hydroxide, calcium hydroxide and cesium hydroxide. The preferred base is triethylamine.

The process as recited above, wherein the base in step (4) is sodium hydroxide, lithium hydroxide, potassium hydroxide, calcium hydroxide, lithium methoxide, sodium methoxide, potassium methoxide, calcium methoxide, lithium ethoxide, sodium ethoxide, potassium ethoxide, lithium tert-butoxide, sodium tert-butoxide, potassium tert-butoxide, sodium carbonate, potassium carbonate, cesium carbonate, sodium bicarbonate, and potassium bicarbonate. The preferred base is lithium hydroxide.

The process as recited above, wherein the acid in step (5) is acetic acid, which is present in amounts between about 2 equivalents and 4 equivalents.

The process as recited above, wherein

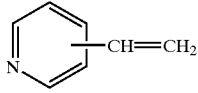

is present in amounts between about 4 equivalents and about 6 equivalents.

The process as recited above, wherein the step (3) reaction initially further comprises the steps of:

(i) breaking the salt compound of formula (c) wherein R$^{9a}$ is O$^-$NHR$_3$$^+$ using citric acid in an aprotic solvent to form a free acid compound of formula (c) wherein R$^{9a}$ is OH; and (ii) reacting the free acid compound of formula (c) with a chlorinating agent in an aprotic solvent to form an acid chloride compound of formula (c) wherein R$^{9a}$ is Cl.

The process as recited above, wherein the chlorinating agent is SOCl$_2$, oxalyl chloride, carbon tetrachloride, and triphenylphosphine dichloride. The preferred chlorinating agent is SOCl$_2$.

Another embodiment of the present invention is a process for preparing a compound of nosyl aziridine of formula

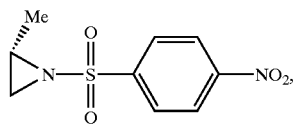

comprising the steps of:

(A) reacting an amino alcohol of formula

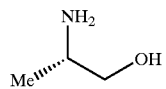

with nosyl chloride in the presence of a base to form a dinosylated compound of formula

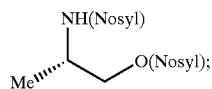

and (B) cyclizing the dinosylated compound in the presence of a non-nucleophilic base in an aprotic solvent to produce the nosyl aziridine.

The process as recited above, wherein the base used for the preparation of nosy aziridine in Step (A) is selected from the group consisting of pyridine, trimethylamine, triethylamine, tripropylamine, tributylamine, quinoline, lutidine, 2,6-dibutylpyridine, tetramethyl piperidine, dimethylaminopyridine, and hexamethyldisilazane. The preferred base is pyridine.

The process as recited above, wherein the non-nucleophilic base used for the preparation of the nosyl aziridine in Step (B) is selected from the group consisting of diisopropylethylamine, trimethylamine, triethylamine, tripropylamine, tributylamine, quinoline, lutidine, 2,6-dibutylpyridine, tetramethyl piperidine, and dimethylaminopyridine. The preferred non-nucleophilic base is diisopropylethylamine.

Another aspect of present invention includes a process for preparing a compound of Formula II,

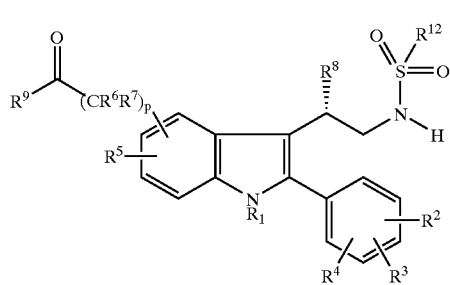

or its pharmaceutically acceptable salt, hydrate or solvate thereof, wherein:

p is: 1–4;

R$^1$ is:
(1) hydrogen,
(2) (C$_1$–C$_6$)-alkyl, or
(3) aryl;

R$^2$, R$^3$, and R$^4$ are independently:
(1) hydrogen,
(2) (C$_1$–C$_6$)-alkyl,
(3) (C$_2$–C$_6$)-alkenyl,
(4) CN,
(5) nitro,
(6) (C$_1$–C$_3$)-perfluoroalkyl,
(7) (C$_1$–C$_3$)-perfluoroalkoxy, or
(8) aryl;

$R^5$ is:
(1) hydrogen,
(2) $(C_1-C_6)$-alkyl,
(3) aryl,
(4) $(C_1-C_3)$-perfluoroalkyl,
(5) CN,
(6) $NO_2$, or
(7) halogen;

$R^6$ and $R^7$ are independently:
(1) hydrogen, or
(2) $(C_1-C_6)$-alkyl;

$R^8$ is:
(1) $(C_1-C_6)$-alkyl; or
(2) aryl;

$R^9$ is:
(1) $(C_1-C_6)$-alkoxy, or
(2) $NHR^{10}R^{11}$, wherein $R^{10}$ and $R^{11}$ are independently:
  (a) hydrogen,
  (b) $(C_1-C_6)$-alkyl, or
  (c) aryl,
  wherein $R^{10}$ and $R^{11}$ taken together form a monocyclic ring, bicyclic ring or bridged ring containing from 3 to 7 carbon atoms, and the ring may be optionally substituted by $R^2$, $R^3$, and $R^4$; and $R^{12}$ is:
(1) $(C_1-C_6)$-alkyl,
(2) halo, wherein halo is F, Cl, Br or I,
(3) $(C_1-C_4)$-perfluoroalkyl,
(4) $(CH_2)_n NMe_3^+$ wherein n is 1 to 6, or
(5) aryl wherein aryl is optionally substituted with one, two, or three substituents selected from the group consisting of $NO_2$, $(C_1-C_6)$-alkyl, and halo as defined above;

comprising the steps of:
reacting a compound of formula (a),

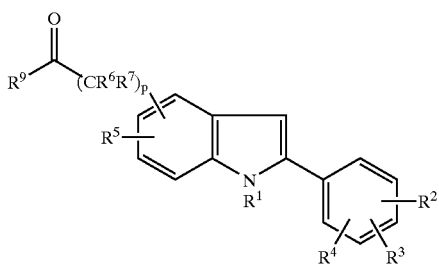

(a)

with an aziridine compound of formula

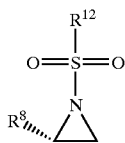

in the presence of a Lewis-acid in an aprotic solvent to produce a compound of formula II.

The process as recited above, wherein the aprotic solvent is selected from the group consisting of: isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof The process as recited above, wherein the aziridine is a nosyl aziridine of formula

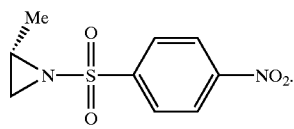

The process as recited above, wherein a temperature range is between about 0° C. and about 60° C.

The process as recited above, wherein the Lewis acid is selected from the group consisting of group consisting of $BF_3$—$OEt_2$, $BX_3$, $SnX_2$, and $SnX_4$ wherein X is halo. The preferred Lewis acid is $BF_3$—$OEt_2$.

Yet another aspect of the present invention involves a process for preparing a compound of Formula III,

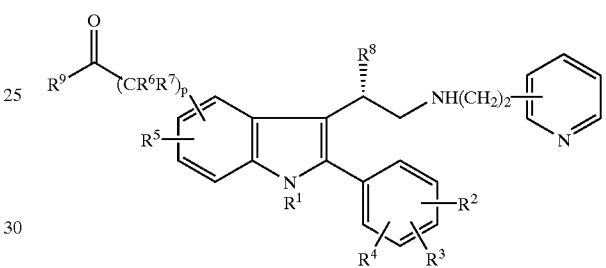

III or its pharmaceutically acceptable salt, hydrate or solvate thereof, wherein:

p is: 1–4;

$R^1$ is:
(1) hydrogen,
(2) $(C_1-C_6)$-alkyl, or
(3) aryl;

$R^2$, $R^3$, and $R^4$ are independently:
(1) hydrogen,
(2) $(C_1-C_6)$-alkyl,
(3) $(C_2-C_6)$-alkenyl,
(4) CN,
(5) nitro,
(6) $(C_1-C_6)$-perfluoroalkyl,
(7) $(C_1-C_6)$-perfluoroalkoxy, or
(8) aryl;

$R^5$ is:
(1) hydrogen,
(2) $(C_1-C_6)$-alkyl,
(3) aryl,
(4) $(C_1-C_3)$-perfluoroalkyl,
(5) CN,
(6) $NO_2$, or
(7) halogen;

$R^6$ and $R^7$ are independently:
(1) hydrogen, or
(2) $(C_1-C_6)$-alkyl;

$R^8$ is:
(1) $(C_1-C_6)$-alkyl; or
(2) aryl;

$R^9$ is:
(1) $(C_1-C_6)$-alkoxy, or
(2) $NHR^{10}R^{11}$, wherein $R^{10}$ and $R^{11}$ are independently:
  (a) hydrogen,
  (b) $(C_1-C_6)$-alkyl, or
  (c) aryl,
  wherein $R^{10}$ and $R^{11}$ taken together form a monocyclic ring, bicyclic ring or bridged ring containing from 3 to 7 carbon atoms, and the ring may be optionally substituted by $R^2$, $R^3$, and $R^4$; and $R^{12}$ is:
(1) $(C_1-C_6)$-alkyl,
(2) halo, wherein halo is F, Cl, Br or I,
(3) $(C_1-C_4)$-perfluoroalkyl,
(4) $(CH_2)_n NMe_3+$ wherein n is 1 to 6, or
(5) aryl wherein aryl is optionally substituted with one, two, or three substituents selected from the group consisting of $NO_2$, $(C_1-C_6)$-alkyl, and halo as defined above;

comprising the steps of:

reacting the compound of formula,

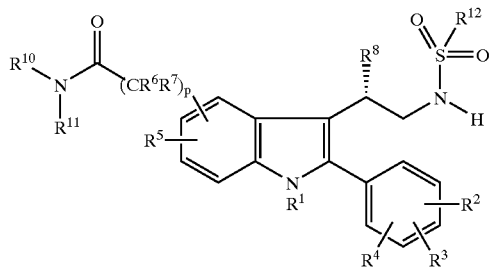

with

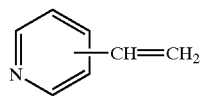

in the presence of an acid in an aprotic solvent to give the compound of Formula III.

The process as recited above, wherein the aprotic solvent is selected from the group consisting of: isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof.

The process as recited above, wherein the acid is selected from the group consisting of triethylamine hydrochloride, and phenol, $(C_1-C_6)$-alkanoic acid, $(C_1-C_6)$-alkanoic diacid, and $(C_1-C_6)$-alkanoic triacid each having a pKa less than 7. The preferred acid is acetic acid.

The process as recited above, wherein the acid is acetic acid, which is present in amounts between about 2 equivalents and 4 equivalents.

The process as recited above comprises the step of deprotecting $-S(O)_2-R^{12}$ group using a mercaptan source and a base in a protic solvent to form the free amine compound of formula,

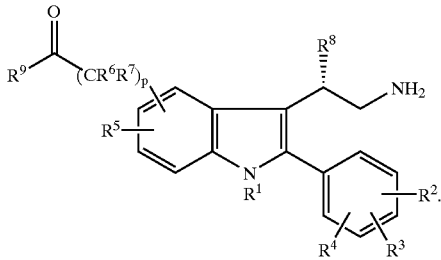

The process as recited above, wherein the mercaptan source is selected from the group consisting of n-dodecanethiol, thiophenol, and mercaptoacetic acid.

The process as recited above, wherein the base is sodium hydroxide, lithium hydroxide, potassium hydroxide, calcium hydroxide, lithium methoxide, sodium methoxide, potassium methoxide, calcium methoxide, lithium ethoxide, sodium ethoxide, potassium ethoxide, lithium tert-butoxide, sodium tert-butoxide, potassium tert-butoxide, sodium carbonate, potassium carbonate, cesium carbonate, sodium bicarbonate, and potassium bicarbonate.

It is further understood that the substituents recited above would include the definitions recited below, and unless otherwise stated or indicated, the definitions shall apply throughout the specification and claims.

As used herein, the term "alkyl" includes those alkyls of a designated number of carbon atoms of either a straight, branched or cyclic configuration. Examples of "alkyl" includes but are not limited to: methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, and the like.

The term "alkenyl" includes hydrocarbon chains of a specified number of carbon atoms of ether a straight or branched configuration and at least one unsaturation, which may occur at any point along the chain, such as ethenyl, propenyl, butenyl, pentenyl, vinyl, allyl, 2-butenyl and the like.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like.

The term "aryl" is defined as phenyl or naphthyl, which may be optionally substituted with one, two or three substituents as set forth in the embodiment recited above.

The term "halogen" or "halo" refer to fluorine, chlorine, bromine and iodine.

The term "amine" refers to primary, secondary, and tertiary amine. Examples of amine include, but are not limited to: methylamine, ethylamine, propylamine, isopropylamine, butylamine, isobutylamine, sec-butylamine, tert-butylamine, dimethylamine, diethylamine, dipropylamine, trimethylamine, triethylamine tripropylamine, tributylamine, and the like.

The term "acid" as used herein includes triethylaminehydrochloride, phenol, $(C_1-C_6)$-alkanoic acid, $(C_1-C_6)$-alkanoic diacid, and $(C_1-C_6)$-alkanoic triacid each having a pKa less than 7.

Methods of preparing the compound of the present invention are illustrated in the following schemes and examples. All substituents are as defined above unless indicated otherwise.

REACTION SCHEME A

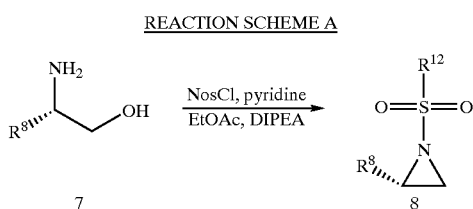

In Reaction Scheme A, the formation of nosyl aziridine, 2-methyl-1-(4-nitrophenylsulfonyl)aziridine (8) is obtained via a two-step, one-pot procedure in a single batch. Amino alcohol (7) is treated with excess nosyl chloride, ClS(O)$_2$C$_6$H$_4$NO$_2$ (herein after NosCl), in the presence of base, such as pyridine, to give a dinosylated intermediate of amino alcohol. Cyclization of the dinosylated amino alcohol is achieved in the presence of a non-nucleophilic base such as diisopropylethylamine (DIPEA) in ethylacetate to give the chiral aziridine product (8), which can be further crystallized from organic solvent such as isopropylaceate (IPAC).

REACTION SCHEME B

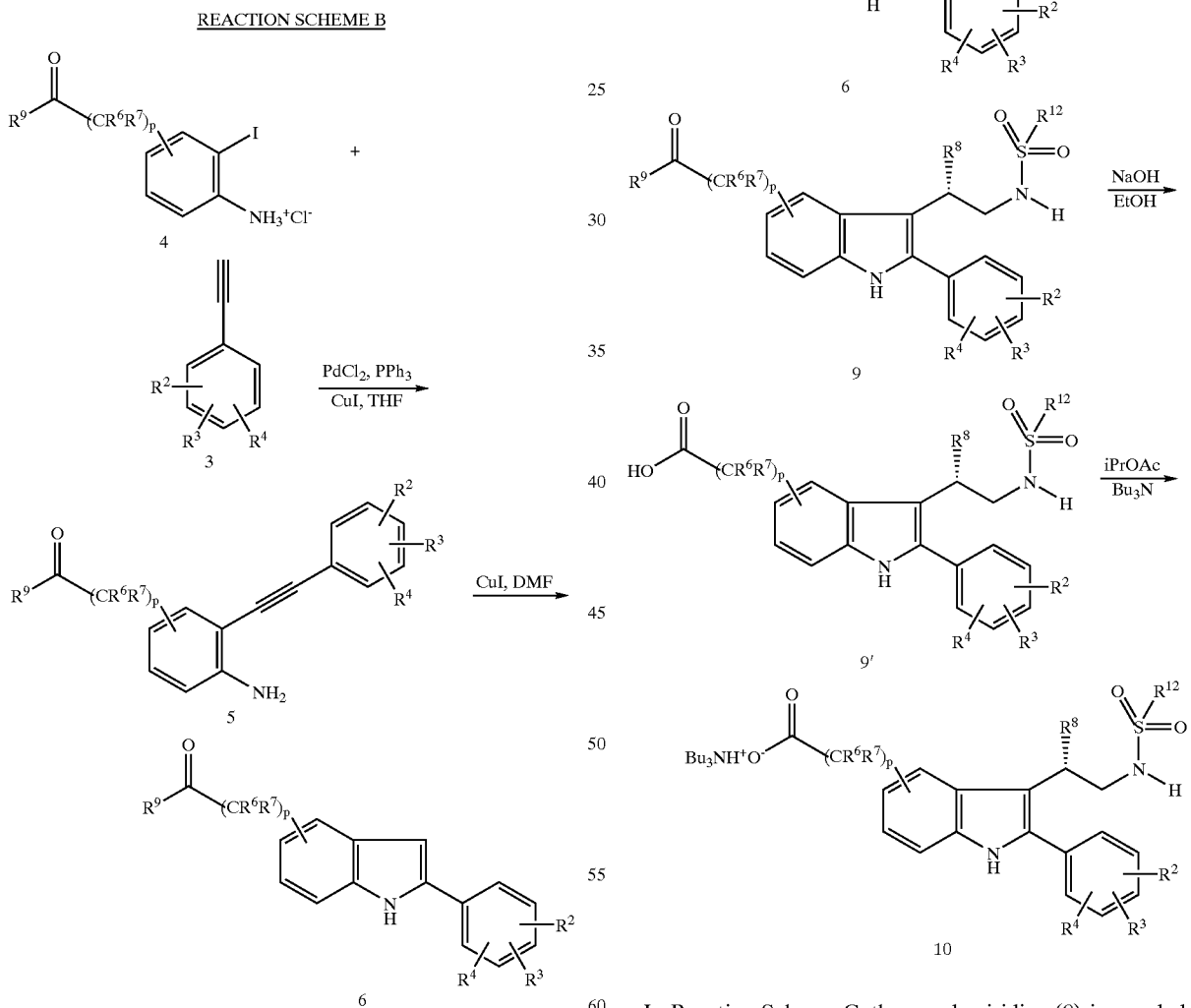

As shown in Reaction Scheme B, iodo aniline of type (4) reacts with aryl acetylene (3) in the presence of palladium catalyst such as PdCl$_2$, phosphine (PPh$_3$), a copper (I) halide such as copper iodide and diisopropylamine or triethylamine in an aprotic solvent such as toluene or tetrahydrofuran (THF) to give diarylacetylene compound (5). Cycloisomerization of diarylacetylene compound (5) in the presence of copper (I) iodide in an aprotic solvent such as dimethylformamide (DMF), toluene or a mixture thereof at a temperature of about 100° C.~150° C., preferably about 120° C. to 140° C. for about 4 to 10 hours to afford arylindole compound (6).

REACTION SCHEME C

In Reaction Scheme C, the nosyl aziridine (8) is coupled with arylindole (6) using stoichiometric boron trifluoride etherate (BF$_3$OEt$_2$) in an aprotic solvent such as toluene at a temperature of about 0° C.~60° C., preferably about 20° C. to 30° C., for about 7 to 24 hours to afford chiral tryptamine compound (9). Saponification of (9) using aqueous sodium hydroxide in a protic solvent such as ethanol gives a corresponding acid (9') of the compound (9). The acid (9')

then reacts with a base such as n-tributylamine in isopropylacetate to afford the tributylamine salt (10) in high yield.

as dodecanethiol or thiophenol in the presence of a base such as lithium hydroxide in a protic solvent such as ethanol to

REACTION SCHEME D

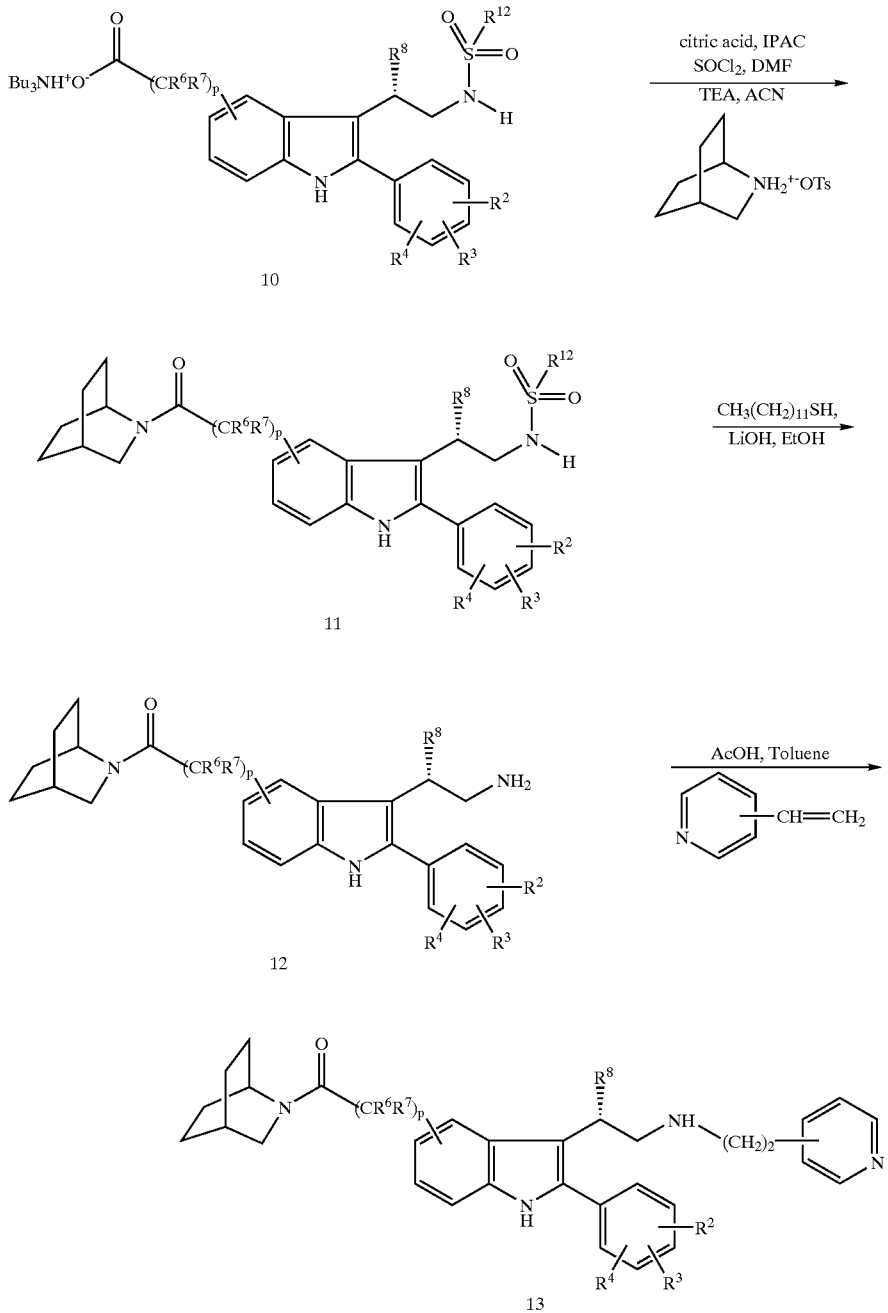

As shown in Reaction Scheme D, salt breaking of (10) using citric acid in isopropylacetate (IPAC) is followed by acid chloride formation in the presence of chlorinating agent such as thionyl chloride (SOCl$_2$) in an aprotic solvent, such as dimethylformamide (DMF). The crude acid chloride solution is then quenched directly into the isoquinuclidine tosylate in acetonitrile (ACN) and triethylamine (TEA) to afford the amide compound (11) in high yield. Deprotection of —SO$_2$R$^{12}$ group (e.g., nosyl group) from the amide (11) can be accomplished using a suitable mercaptan source such yield the primary amine compound (12). The extracted amine compound (12) is then allowed to react with vinyl pyridine (about 4 to 6 equivalents, preferably about 5 equivalents) in the presence of acid catalyst such as acetic acid (about 2 to 4 equivalents, preferably about 3 equivalents) in an aprotic solvent such as toluene at a temperature about 60° C. to 100° C., preferably at about 80° C., for about two to four hours to afford the final compound of chiral tryptamine (13). The final compound (13) can be further crystallized in organic solvent such as ethyl acetate.

The following examples illustrate the preparation of the compound of Formula I, and as such not to be considered as limiting the invention set forth in the claims appended hereto.

EXAMPLE 1

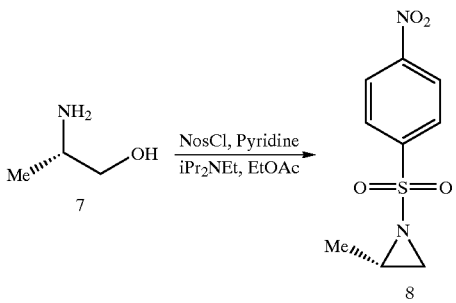

A 100 gallon glass-lined vessel, fitted with mechanical stirrer, addition funnel, nitrogen inlet and temperature probe, was charged with nosylchloride (52.7 kg) and acetonitrile (75L) at room temperature under nitrogen. The slurry was cooled to about 0° C. A solution of L-alaninol (7) (7.5 kg) in pyridine (32L) was added over about an hour maintaining the reaction temperature less than 10° C. during the addition, and then the mixture was aged for about two hours at about 3° C. to 5° C. Ethyl acetate (188L) and water (75L) were added and the phases were mixed. The lower aqueous layer was removed and the organic layer was washed with 1M citric acid (2×37.5L) and water (37.5L). The organic layer was cooled to about 15° C. and water (37.5L) was added. Hunig's base (N,N-diisopropylethylamine) (27L) was added for over 30 minutes. The two-phase mixture was aged at 20° C. for about an hour to complete the cyclization, and then the lower aqueous layer was removed and extracted with ethyl acetate (37.5L). The combined organic solutions were washed with 1M citric acid (2×37.5L) and water (2×37.5L). The organic layer was dried by concentration at reduced pressure and temperature at about 15° C.~20° C. with concurrent addition of isopropylacetate (IPAC) to maintain the constant volume at about 100L. The solvent switch was completed when EA level was <5% by GC or HPLC analysis. The slurry was cooled to about 3° C. for an hour and then filtered. The cake was washed with IPAC (30L) and the solid was dried in air, which afforded about 84% isolated yield for the compound (8) (23.7 kg, 97 wt %).

EXAMPLE 2

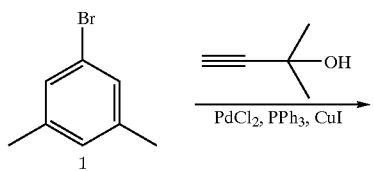

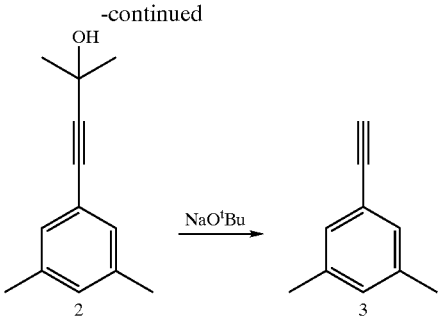

A 100 gallon glass-lined vessel fitted with nitrogen inlet, stirrer, temperature probe and condenser was charged with bromo xylene (1) (22.2 Kg) followed by diethylamine (33.3L), heptane (44L) and MYBENOL (2-methyl 3-butyn-2-ol) (16.7L). A mixture of palladium chloride (123 g), triphenylphosphine (934 g) and copper (I) iodide (222 g) was added in one portion at about 20° C. The mixture was warmed to reflux and aged for about 2 hours, and then heptane (90L) was added. The mixture was cooled to about 40° C. and concentrated at reduced pressure and temperature at about 30° C. to 40° C. to remove 70L of distillate. Heptane (45L) was added and the slurry was cooled to about 5° C. The slurry was aged for an hour and then filtered. The cake was washed with heptane (45L×2) and the filtrates were combined. The combined filtrates were then assayed for acetylenic alcohol (2) (assay: 22.4 kg, 99%). Sodium tert-butoxide (2.22 kg) and Darco-G60 (2.22 kg) were added to the acetylenic alcohol solution (2). The slurry was warmed to reflux and heptane (45L) was distilled off over about 45 minutes to an hour. The reaction mixture was then cooled to about 5° C., aged for about two hours, and then filtered. The cake was washed with heptane (23L) and the dark filtrates was combined and assayed for the compound (3) (assay: 13.5 kg, 94%).

EXAMPLE 3

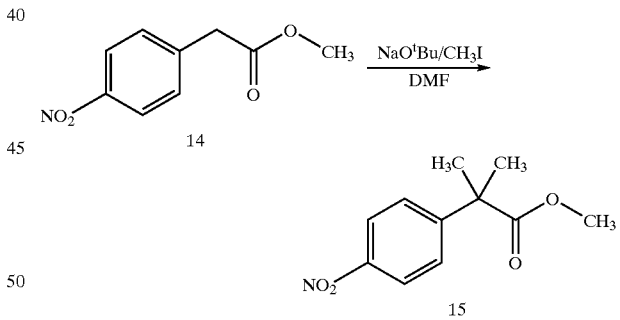

A 100L round-bottom flask fitted with mechanical stirrer, temperature probe, addition funnel, and nitrogen inlet was charged with dry diemethylformamide (DMF) (50L). The DMF was cooled to about 0° C. and sodium tert-butoxide (2.5 kg) was added in one portion. The cloudy solution was cooled again to about 5° C. Methyl-4-nitrophenylacetate (14) (5.0 kg) was added in one portion. The purple slurry was cooled to about 5° C. Methyl iodide (1.6L) was added for an hour while maintaining the reaction temperature at less than about 10° C. The slurry was then aged for about 15 minutes while cooling to about 5° C. A second charge of sodium tert-butoxide (2.5 kg) was added to the batch in one portion. Methyl iodide (1.6L) was added for about 40 minutes while maintaining the batch temperature at less than about 10° C. The slurry was aged for about 20 minutes at about 5° C. to 10° C. A third charge of sodium tert-butoxide (0.25 kg) was added to the batch in one portion. Methyl iodide (0.3L) was added for about 5 minutes while maintaining the batch temperature at less than about 10° C. The slurry was aged for about 20 minutes at about 5° C. to 10° C. Water (50L) containing acetic acid (0.83L) was added for about 20 minutes at about 5° C. to 10° C. followed by isopropyl acetate (20L). The phases were well mixed and the lower aqueous layer was removed. The aqueous layer was re-extracted with isopropylacetate (10L) and then the organics were combined. The organics were washed with 0.5N HCl (2×10L) and brine (10L) to give the compound (15) (assay yield: 5.5 kg, 96%).

EXAMPLE 4

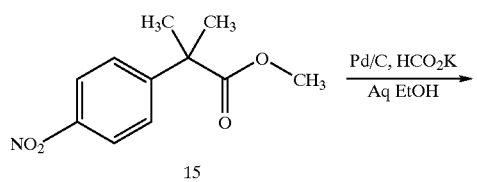

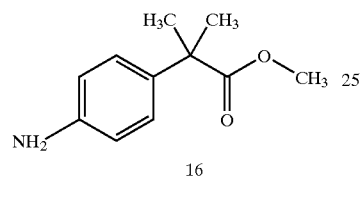

A 100L round-bottom flask fitted with stirrer, addition funnel and nitrogen inlet was charged with an ethanolic solution dimethyl ester (5.5 kg by assay). To the solution was added a slurry of 10% palladium on carbon (50% water wet, 200 g) in water (1.0L). The resultant slurry was stirred and warmed to about 45° C. A solution of potassium formate in water (10.35 kg in 28L) was added for about two hours, and then the reaction mixture was stirred at about 60° C. to 70° C. for about an hour. The slurry was then cooled to about 15° C. and filtered through a pad of solka floc (100 g). The cake was washed with 50%v/v aqueous ethanol (30L) and the filtrates were combined (assay for (16): 4.5 kg, 95%).

EXAMPLE 5

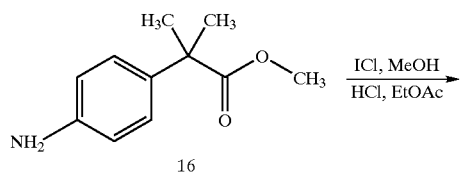

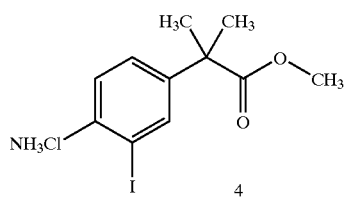

A 100L round-bottom flask fitted with stirrer, addition funnel and nitrogen inlet was charged with aqueous ethanolic solution aniline (4.5 kg by assay). To the solution was added concentrated HCl (1.1L) to adjust pH to about 5.7. The solution was cooled to about 10° C. A solution of iodine monochloride in HCl (50 wt % nominal, 6.6L) was added for about an hour with concurrent addition of 25 wt % sodium hydroxide to maintain pH at about 5.0 to 5.5. The reaction mixture was then stirred at about 15° C. to 20° C. for an hour. Upon completion (<2.0 A% SM remaining), IPAC (15L) was added and the pH was adjusted to about 7 to 8 by adding 25 wt % sodium hydroxide solution. The phases were well mixed and allowed to separate. The lower aqueous layer was removed. IPAC (15L) was added to the upper layer and the combined organics were washed with 20 wt % NaCl (3×10L). The IPAC solution was concentrated with concurrent addition of IPAC (15° C. L) to dry the solution to a Kf of <400 μg/ml. The IPAC/HCl solution was added to the product IPAC solution at about 20° C. to 25° C. for about 30 minutes. The resultant slurry of hydrochloride salt was aged for about 10 minutes at about 20° C. and then cooled to about 5° C. for an hour. The slurry was filtered and washed with IPAC (20L) and dried in nitrogen stream overnight. (Yield for (4): 90%).

Preparation of IPAC/HCl Solution:

A 50L round-bottom flask was charged with IPAC (15L) and methanol (2.5L). The solution was cooled to about 10° C. and acetyl chloride (2.5L) was added over for an hour. The resultant solution was stirred at room temperature for about 30 minutes before use.

EXAMPLE 6

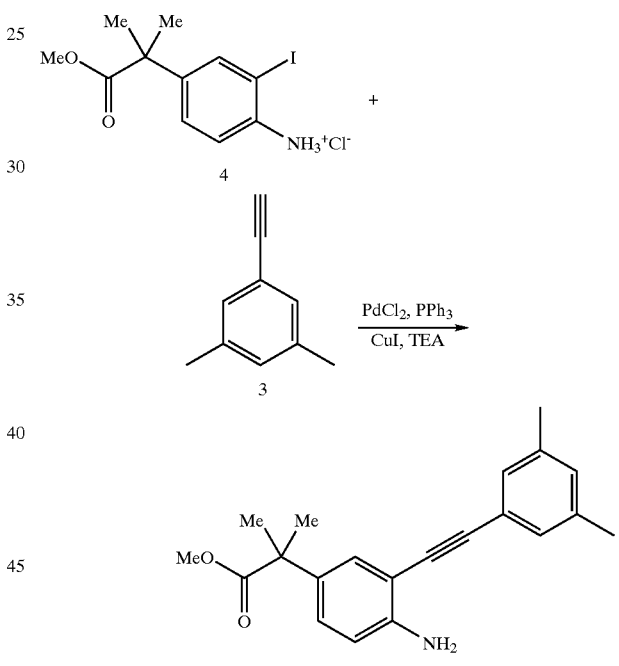

A 100 gallon vessel fitted with nitrogen inlet, stirrer, temperature probe and addition funnel was inerted with nitrogen. Toluene (155L) and iodoaniline (4) (32 kg) were added. Triethylamine (TEA) (37.8L) was added for about 10 minutes at room temperature followed by water (78L). A mixture of palladium chloride (159 g), triphenylphosphine (720 g) and copper (I) iodide (342 g) was added in one portion at about 28° C. The mixture was warmed to about 70° C. and the acetylene solution (3) (153L) was added for an hour. The reaction mixture was aged at about 70° C. to 75° C. for about an hour. The mixture was then cooled to room temperature and the lower aqueous layer was removed. The organic layer was washed with 5% aqueous ammonium hydroxide solution (2×17L) and D.I. water (10L). The organic layer was concentrated under reduced pressure to approximately 122L (yield for (5): 95%). The solution was used is to prepare 2-arylindole compound (6).

EXAMPLE 7

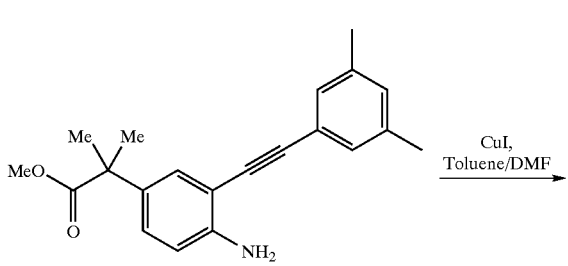

A 100 gallon glass-lined vessel was charged with a solution of Castro ester (5) in toluene (27.9 kg) and DMF (110L). Copper (I) Iodide (8.3 kg) was added and the slurry warmed to reflux for about 7 hours at about 120° C. to 140° C. Upon completion, the reaction mixture was cooled to about 5° C. and aged for about 30 minutes. The slurry was filtered and the cake washed with toluene (50L). The organics were washed with 5% ammonium hydroxide solution (2×60L), water (60L), 0.1 M HCl (60L) and 15% aqueous brine (60L). The wet solution (Kf>700 μg/ml) was concentrated at about 30° C. to 40° C. under vacuum to dry the solution. Silica gel (25 kg) was added to the batch at about 20° C. and the slurry stirred for at least 30 minutes at about 20° C. The slurry was filtered through silica gel (25 kg) and the cake washed with toluene (230L). The filtrate was then concentrated under vacuum to about 60L. Heptane (60L) was added at about 40° C. and the solution seeded with indole (2 g). The slurry was aged at about 40° C. for about 30 minutes and then cooled to about 20° C. Heptane (200L) was added for about 30 minutes. The slurry was cooled to about 5° C. and aged for about two hours. The slurry was filtered and the cake was washed with heptane (50L). The cake (6) was dried at room temperature for overnight (yield 21.7 kg, 98 wt %; 21.3 kg pure basis, 76%).

EXAMPLE 8

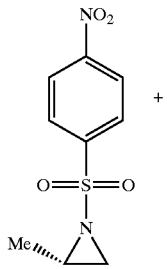

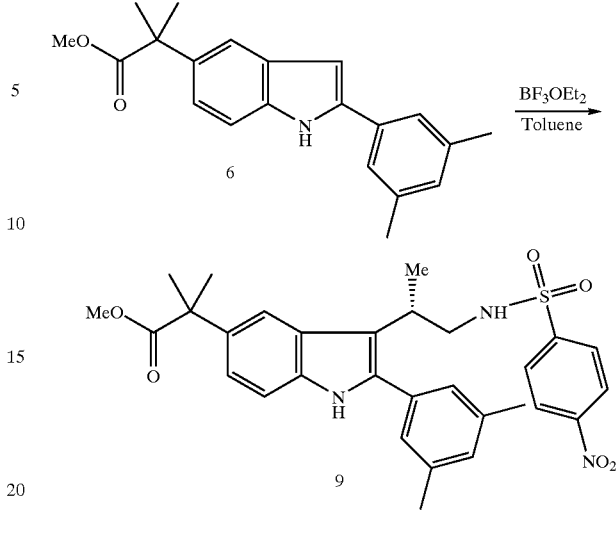

The aryl indole (6) (11.46 kg), nosyl aziridine (8) (10.48 kg) and toluene (50L) were charged into a 100-gallon vessel under a nitrogen atmosphere. Boron trifluoride etherate (5.46 kg) was added over for an hour at about 20° C. to 25° C. The reaction was aged at about 20° C. to 25° C. for about 10 to 20 hours. The reaction mixture was added to a stirred mixture of ethyl acetate (70L) and 2M KHCO$_3$ (70L) for about 30 minutes. The lower aqueous layer was removed and the organic layer was washed with water (40L). The organic layer was concentrated to about 20% volume under reduced pressure (up to 50° C.) and then ethanol (50L) was added. The mixture was concentrated and ethanol was added to complete solvent switch (<1% v/v toluene). The final volume was adjusted to about 65L by distillation under reduced pressure. The product solution (9) was used in the preparation of amine salt (yield: 89–92%).

EXAMPLE 9

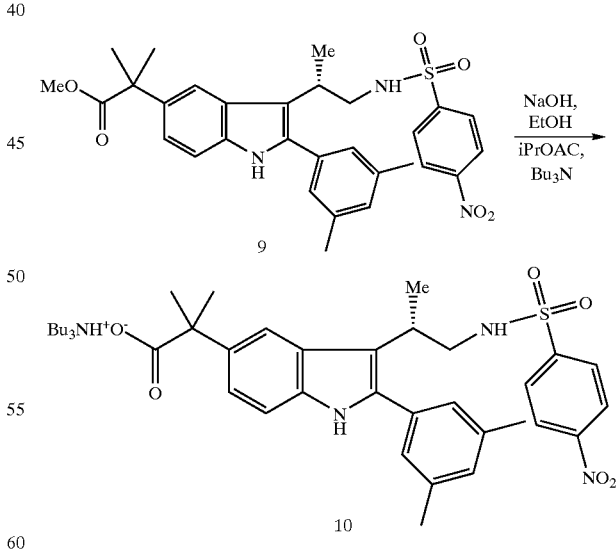

Sodium hydroxide (50%w/w aqueous, 12.6 kg) was added to water (110L). The resultant solution was added to the slurry of ester (9) in ethanol at about 20° C. for about 30 minutes. The slurry was warmed to gentle reflux for about an hour. The reaction mixture was then cooled to about 20° C. and added to a slurry of citric acid (20 kg) in water (50L)

and IPAC (100L). The lower aqueous layer was removed and the organic layer was washed with water (2×10L). The organic layer was then concentrated under reduced pressure and temperature at about 25° C. to 40° C. with concurrent addition of IPAC until the solution Kf was less than about 300 μg/ml. The resultant IPAC solution (100L total volume) of the acid (>96% yield) was stirred at about 20° C. under nitrogen and tri-n-butylamine (9.0L) was added for about 15 minutes. The resultant slurry was aged at room temperature for about 30 minutes, and then cooled to about 5° C. for an hour. The slurry was then filtered and the yellow cake was washed with pre-cooled IPAC (25L). The cake (10) was dried in nitrogen flow for overnight. (yield: 22.4 kg, 99.3 wt %; 21.7 kg pure basis, 94%).

EXAMPLE 10

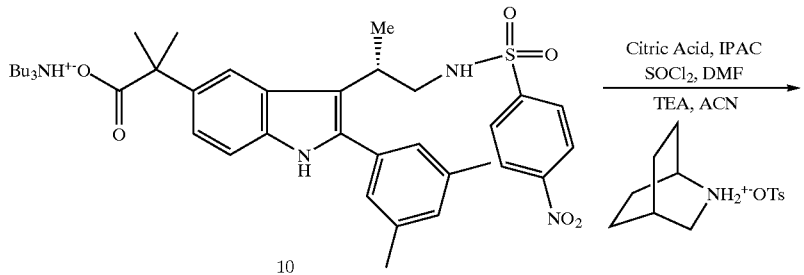

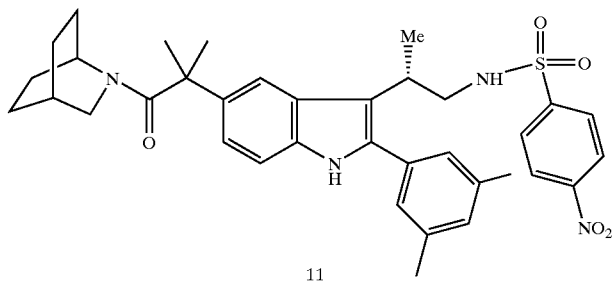

A 100L separator was charged with acid tributylamine salt (10) (15.5 kg) and IPAC (60L) at room temperature under a nitrogen atmosphere. The slurry was stirred and 2M citric acid (23L) was added for about 2 minutes. The lower aqueous layer was removed and the organic layer was washed with 2M citric acid (11L) and water (12L×2). The organic layer was concentrated under reduced pressure and temperature at about 30° C. to 40° C. with concurrent addition of IPAC to dry the solution to less than 200 μg/ml. DMF (100 mL) was added followed by thionyl chloride (2.32L). The solution was then aged at about 25° C. to 30° C. for about one to two hours. The reaction mixture was then concentrated to about 40L. A separate 100L flask was charged with acetonitrile (12L), amine tosylate (7.82 kg) and triethylamine (9.5L). The slurry was stirred at about 20° C. for about 30 minutes prior to addition of the acid chloride solution. The acid chloride solution was added to the amine slurry over for an hour, and the mixture was aged for about 30 minutes at about 25° C. Water (25L) was added and the phases were well mixed. The lower aqueous layer was removed and the organic layer was washed with 2M citric acid (20L) and water. The organic layer was then assayed for the amide compound (11) (yield: 12.5 kg, 97%).

EXAMPLE 11

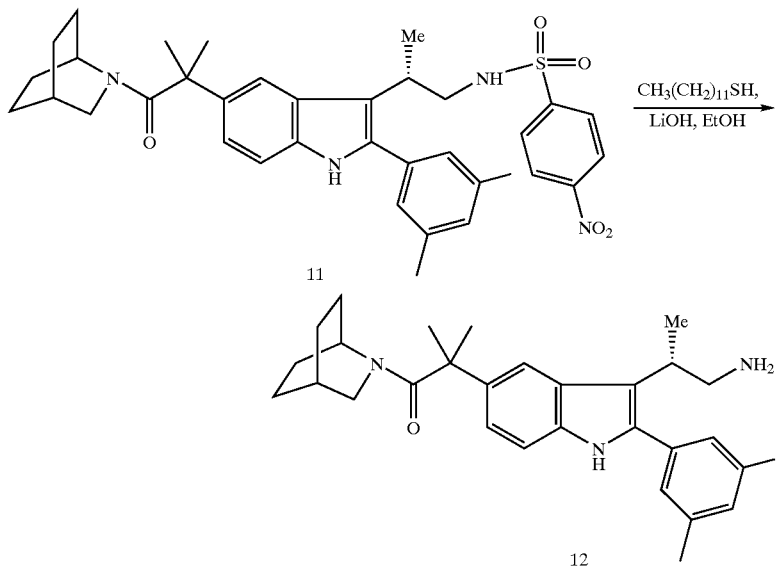

In a 100L round-bottom flask, the amide solution (11) in IPAC (50L) was solvent switched to ethanol under vacuum below 35° C. Dodecanethiol (8.04 kg) was added followed by lithium hydroxide monohydrate (1.67 kg). The batch was heated to about 50° C. for about an hour and then cooled to room temperature. The batch was concentrated to about 40L and toluene (25L) was added followed by aqueous citric acid (2M, 30L). The toluene layer was removed and additional toluene (25L) was added followed by ethanol (4L). The toluene layer was removed and additional toluene (30L) was added followed by pH adjustment with 50% NaOH (about 8–9L). The batch was heated to about 50° C. Water (10L) was added and the aqueous layer was removed. The primary amine product (12) was used to prepare the final compound (13).

EXAMPLE 12

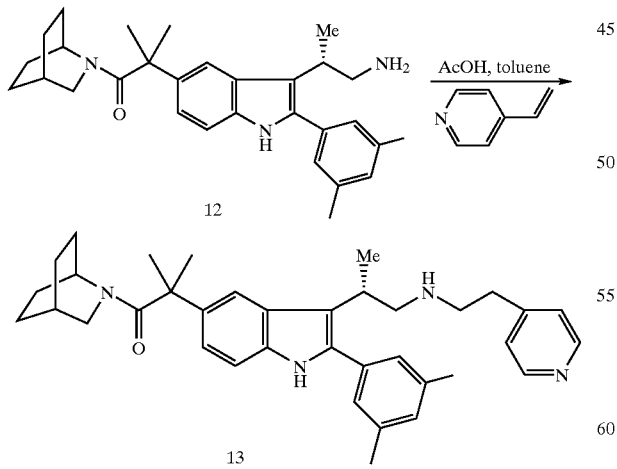

In a 100L separator, the amine solution (12) in toluene (190 mg/mL, 45L) was heated to about 55° C. under nitrogen. 4-Vinyl pyridine (7.84 kg) was added followed by acetic acid (2.67L). The batch was then heated to about 80° C. and aged for about two hours. The batch was cooled to about 50° C. and washed with aqueous sodium hydroxide (2.5M, 20L final pH 13.0–14.0). The aqueous layer was separated and the organic layer was washed with water (16L×2) at about 50° C. The batch was then concentrated and solvent was switched to methanol and then to ethyl acetate. The mixture was seeded and was allowed to age for about 24 hours prior to filtering. The cake was washed with ethyl acetate (0° C., 15L) to give the final product (13) (yield 80%).

What it is claimed is:

1. A process for preparing a compound of Formula I,

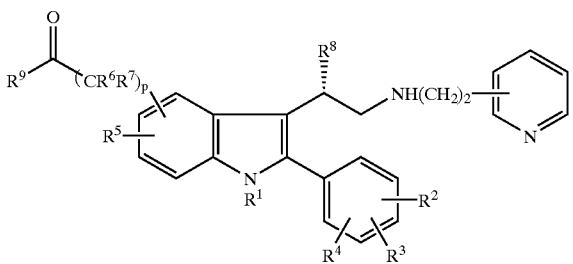

or its pharmaceutically acceptable salt, hydrate or solvate thereof, wherein:

p is: 1–4;

$R^1$ is:
(1) hydrogen,
(2) $(C_1-C_6)$-alkyl, or
(3) aryl;

$R^2$, $R^3$, and $R^4$ are independently:
(1) hydrogen,
(2) $(C_1-C_6)$-alkyl,
(3) $(C_2-C_6)$-alkenyl,
(4) CN,
(5) nitro,
(6) $(C_1-C_3)$-perfluoroalkyl,
(7) $(C_1-C_3)$-perfluoroalkoxy, or
(8) aryl;

$R^5$ is:
(1) hydrogen,
(2) $(C_1-C_6)$-alkyl,
(3) aryl,
(4) $(C_1-C_3)$-perfluoroalkyl,
(5) CN,
(6) $NO_2$, or
(7) halogen;

$R^6$ and $R^7$ are independently:
(1) hydrogen, or
(2) $(C_1-C_6)$-alkyl;

$R^8$ is:
(1) $(C_1-C_6)$-alkyl; or
(2) aryl; and $R^9$ is:
(1) $(C_1-C_6)$-alkoxy, or
(2) $NHR^{10}R^{11}$, wherein $R^{10}$ and $R^{11}$ are independently:
 (a) hydrogen,
 (b) $(C_1-C_6)$-alkyl, or
 (c) aryl,
 wherein $R^{10}$ and $R^{11}$ taken together form a monocyclic ring, bicyclic ring or bridged ring containing from 3 to 7 carbon atoms, and the ring may be optionally substituted by $R^2$, $R^3$, and $R^4$; and $R^{12}$ is:
(1) $(C_1-C_6)$-alkyl,
(2) halo, wherein halo is F, Cl, Br or I,
(3) $(C_1-C_4)$-perfluoroalkyl,
(4) $(CH_2)_n NMe_3^+$ wherein n is 1 to 6, or
(5) aryl wherein aryl is optionally substituted with one, two, or three substituents selected from the group consisting of $NO_2$, $(C_1-C_6)$-alkyl, and halo as defined above;

comprising the steps of:

(1) reacting a compound of formula (a),

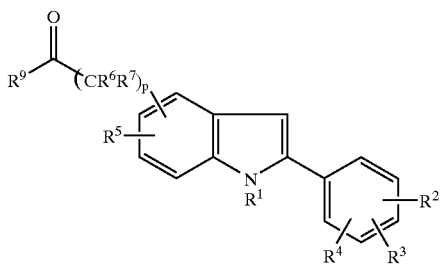

with an aziridine compound of formula

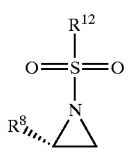

in the presence of a Lewis-acid in an aprotic solvent to produce a compound of formula (b)

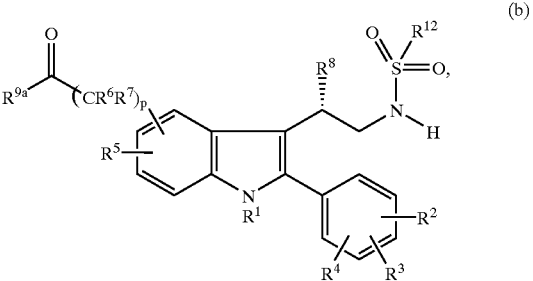

wherein $R^{9a}$ is $(C_1-C_6)$-alkoxy, hydrolyzing the compound of formula (b) in the presence of a base and a protic solvent to give an acid form of the compound of formula (b) wherein $R^{9a}$ is hydroxyl;

(2) reacting the acid form of the compound of formula (b) with an amine in an aprotic solvent to produce a compound of formula (c)

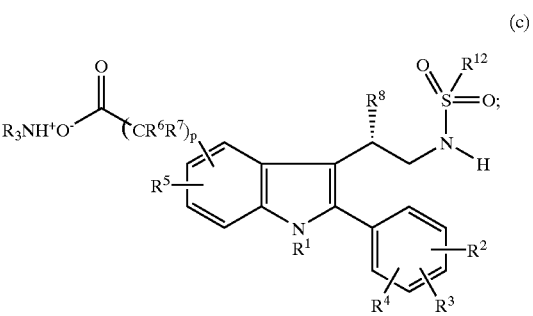

(3) reacting the compound of formula (c) with amine, $NHR^{10}R^{11}$ in the presence of a base in an aprotic solvent to give an amide compound of formula (d),

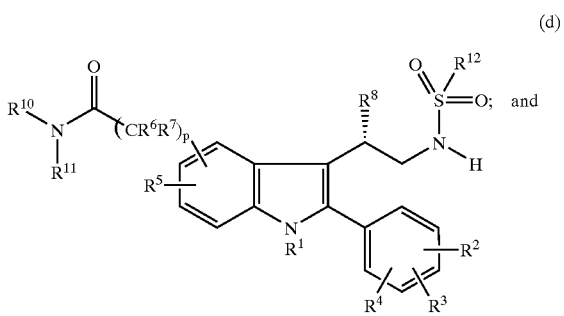

(4) reacting the compound of formula (d) with

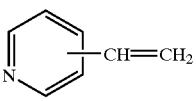

in the presence of an acid in an aprotic solvent to give the compound of Formula I.

2. The process of claim 1, wherein the aprotic solvent is selected from the group consisting of: isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof.

3. The process of claim 2, wherein the aziridine is a nosyl aziridine of formula

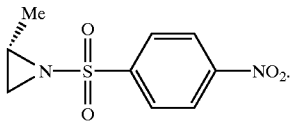

4. The process of claim 3, wherein a temperature range for the step (1) reaction is between about 0° C. and about 60° C.

5. The process of claim 4, wherein the Lewis acid in step (1) is selected from the group consisting of group consisting of $BF_3$—$OEt_2$, $BX_3$, $SnX_2$, and $SnX_4$ wherein X is halo.

6. The process of claim 5, wherein the base in step (1) is selected from the group consisting of sodium hydroxide, lithium hydroxide, potassium hydroxide, calcium hydroxide, lithium methoxide, sodium methoxide, potassium methoxide, lithium ethoxide, sodium ethoxide, potassium ethoxide, lithium tert-butoxide, sodium tert-butoxide, and potassium tert-butoxide.

7. The process of claim 6, wherein the protic solvent is selected from the group consisting of $(C_1-C_6)$-alcohol, $H_2O$ or mixtures thereof.

8. The process of claim 7, wherein the amine in step (2) is $NH_3$, $NHR_2$ or $NR_3$ wherein R is $(C_1-C_6)$-alkyl, which is selected from the group consisting of methylamine, ethylamine, propylamine, isopropylamine, butylamine, isobutylamine, sec-butylamine, n-tributylamine, tert-butylamine, dimethylamine, diethylamine, dipropylamine, trimethylamine, and triethylamine, tripropylamine, and tributylamine.

9. The process of claim 8, wherein the base in step (3) is selected from the group consisting of tert-butylamine, trimethylamine, triethylamine, tripropylamine, and tributylamine, tetramethyl piperidine, hexamethyldisilazane, sodium carbonate, potassium carbonate, cesium carbonate, sodium bicarbonate, potassium bicarbonate, sodium hydroxide, potassium hydroxide, calcium hydroxide and cesium hydroxide.

10. The process of claim 9, wherein the acid in step (4) is selected from the group consisting of triethylamine hydrochloride, phenol, $(C_1-C_6)$-alkanoic acid, $(C_1-C_6)$-alkanoic diacid, and $(C_1-C_6)$-alkanoic triacid each having a pKa less than 7.

11. The process of claim 10, wherein

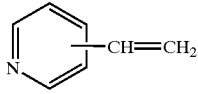

is present in amounts between about 4 equivalents and about 6 equivalents.

12. The process of claim 1, wherein the step (3) reaction initially further comprises the steps of:
    (i) breaking the salt compound of formula (c) wherein $R^{9a}$ is O—$NHR_3^+$ using citric acid in an aprotic solvent to form a free acid of formula (c) wherein $R^{9a}$ is OH; and
    (ii) reacting the free acid compound of formula (c) with a chlorinating agent in an aprotic solvent to form an acid chloride compound of formula (c) wherein $R^{9a}$ is Cl.

13. The process of claim 12, wherein the chlorinating agent is $SOCl_2$, oxalyl chloride, carbon tetrachloride, and triphenylphosphine dichloride.

14. The process of claim 1, wherein the step (4) reaction initially further comprises deprotecting —$S(O)_2$—$R^{12}$ group of the compound of formula (d) using a mercaptan source and a base in a protic solvent to form the free amine compound of formula (d),

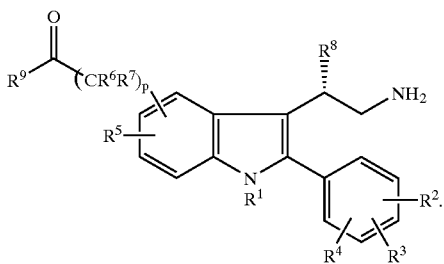

15. The process of claim 14, wherein the mercaptan source is selected from the group consisting of n-dodecanethiol, thiophenol, and mercaptoacetic acid.

16. The process of claim 15, wherein the base is sodium hydroxide, lithium hydroxide, potassium hydroxide, calcium hydroxide, lithium methoxide, sodium methoxide, potassium methoxide, calcium methoxide, lithium ethoxide, sodium ethoxide, potassium ethoxide, lithium tert-butoxide, sodium tert-butoxide, potassium tert-butoxide, sodium carbonate, potassium carbonate, cesium carbonate, sodium bicarbonate, and potassium bicarbonate.

17. A process for preparing a compound of Formula I'

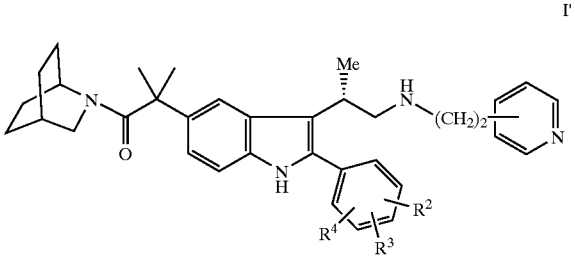

or pharmaceutically acceptable salt, hydrate, or solvate thereof, wherein $R^2$, $R^3$, and $R^4$ are independently hydrogen or $(C_1-C_6)$-alkyl; comprising the steps of:
    (1) reacting a compound of formula (a)'

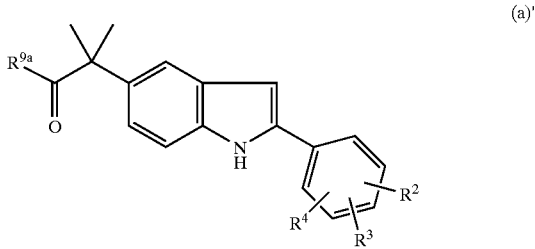

wherein $R^{9a}$ is $OCH_3$, with a nosyl aziridine of formula

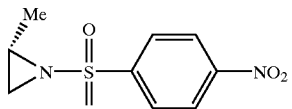

in the presence of a Lewis-acid in an aprotic solvent to produce a compound of formula (b)'

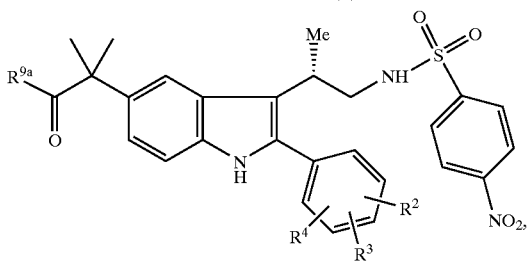

hydrolyzing the compound of formula (b)' in the presence of a base and a protic solvent to give an acid form of the compound of formula (b)' wherein $R^{9a}$ is hydroxyl;

(2) reacting the acid form of the compound of formula (b)' with n-tributylamine in an aprotic solvent to produce a compound of formula (c)'

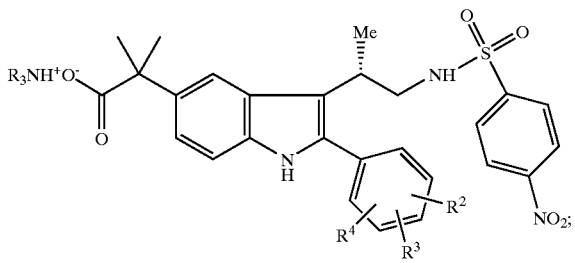

(3) reacting the compound of formula (c)' with isoquinuclidine in the presence of a base in an aprotic solvent to give an amide isoquinuclidinyl compound of formula (d)'

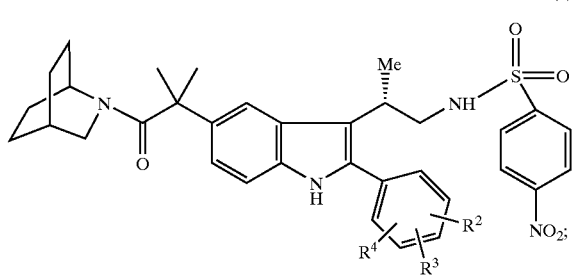

(4) deprotecting nosyl protected amine of formula (d)' in the presence of n-dodecanethiol, a base, and a protic solvent to give a free amine of formula (d)",

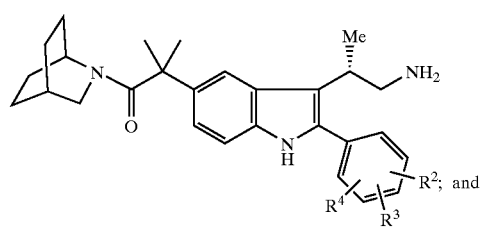

(5) reacting the free amine of formula (d)" with

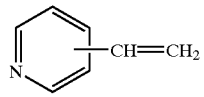

in the presence of an acid in an aprotic solvent to give the compound of Formula I'.

18. The process of claim 17, wherein the aprotic solvent is selected from the group consisting of isopropylacetate, ethylacetate, tetrahydrofuran, acetonitrile, toluene, pentane, hexane, benzene, dimethylacetamide, dimethylformamide, N-methylpyrrolidinone, diethyl ether, dichloromethane, chloroform, ethylacetate, and mixtures thereof.

19. The process of claim 18, wherein a temperature range for the step (1) reaction is between about 0° C. and about 60° C.

20. The process of claim 19, wherein the Lewis acid in step (1) is selected from the group consisting of $BF_3$—$OEt_2$, $BX_3$, $SnX_2$, and $SnX_4$ wherein X is halo.

21. The process of claim 20, wherein the base in step (1) is selected from the group consisting of sodium hydroxide, lithium hydroxide, potassium hydroxide, calcium hydroxide, lithium methoxide, sodium methoxide, potassium methoxide, lithium ethoxide, sodium ethoxide, potassium ethoxide, lithium tert-butoxide, sodium tert-butoxide, and potassium tert-butoxide.

22. The process of claim 21, wherein the protic solvent is selected from the group consisting of $(C_1$–$C_6)$-alcohol, $H_2O$ or mixtures thereof.

23. The process of claim 22, wherein the base in step (3) is selected from the group consisting of tert-butylamine, trimethylamine, triethylamine, tripropylamine, and tributylamine, tetramethyl piperidine, hexamethyldisilazane, sodium carbonate, potassium carbonate, cesium carbonate, sodium bicarbonate, potassium bicarbonate, sodium hydroxide, potassium hydroxide, calcium hydroxide and cesium hydroxide.

24. The process of claim 23, wherein the base in step (4) is sodium hydroxide, lithium hydroxide, potassium hydroxide, calcium hydroxide, lithium methoxide, sodium methoxide, potassium methoxide, calcium methoxide, lithium ethoxide, sodium ethoxide, potassium ethoxide, lithium tert-butoxide, sodium tert-butoxide, potassium tert-butoxide, sodium carbonate, potassium carbonate, cesium carbonate, sodium bicarbonate, and potassium bicarbonate.

25. The process of claim 24, wherein the acid in step (5) is acetic acid, which is present in amounts between about 2 equivalents and 4 equivalents.

26. The process of claim 25, wherein

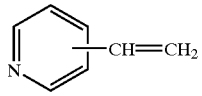

is present in amounts between about 4 equivalents and about 6 equivalents.

27. The process of claim 17, wherein the step (3) reaction initially further comprises the steps of:

(i) breaking the salt compound of formula (c) wherein $R^{9a}$ is $O^-NHR_3^+$ using citric acid in an aprotic solvent to form a free acid compound of formula (c) wherein $R^{9a}$ is OH; and (ii) reacting the free acid compound of formula (c) with a chlorinating agent in an aprotic solvent to form an acid chloride compound of formula (c) wherein $R^{9a}$ is Cl.

28. The process of claim 27, wherein the chlorinating agent is $SOCl_2$, oxalyl chloride, carbon tetrachloride, and triphenylphosphine dichloride.

* * * * *